United States Patent
Tang et al.

(10) Patent No.: US 8,247,589 B2
(45) Date of Patent: Aug. 21, 2012

(54) ORGANIC SILICON PHOSPHATE AND FABRICATION METHOD THEREOF

(75) Inventors: Shang-Wei Tang, Taipei (TW); Hsueh-Tso Lin, Taipei (TW); Kuan-Ching Chen, Taipei (TW); Dick Zhong, Taipei (TW)

(73) Assignee: Grand Tek Advance Material Science Co., Ltd., Taipei (TW)

( * ) Notice: Subject to any disclaimer, the term of this patent is extended or adjusted under 35 U.S.C. 154(b) by 285 days.

(21) Appl. No.: 12/776,904

(22) Filed: May 10, 2010

(65) Prior Publication Data
US 2011/0160475 A1 Jun. 30, 2011

(30) Foreign Application Priority Data
Dec. 25, 2009 (TW) ................ 98144938 A

(51) Int. Cl.
| C07F 9/06 | (2006.01) |
| C07F 9/08 | (2006.01) |
| C07F 9/09 | (2006.01) |
| C07F 9/02 | (2006.01) |

(52) U.S. Cl. ........................ 556/405
(58) Field of Classification Search ............ None
See application file for complete search history.

(56) References Cited

U.S. PATENT DOCUMENTS
| 6,319,432 B1 | 11/2001 | Harrod et al. |
| 6,605,736 B1 | 8/2003 | Nakamura et al. |
| 6,605,737 B1 | 8/2003 | Nakamura et al. |
| 6,613,928 B1 | 9/2003 | Nakamura et al. |

FOREIGN PATENT DOCUMENTS
| JP | 2000-256378 | 9/2000 |

OTHER PUBLICATIONS
Machine translation of Norihisa et al. (JP 2000-256378).*

\* cited by examiner

*Primary Examiner* — Yevegeny Valenrod
(74) *Attorney, Agent, or Firm* — Muncy, Geissler, Olds & Lowe, PLLC

(57) ABSTRACT

The invention provides an organic silicon phosphate and fabrication method thereof. The organic silicon phosphate has formula (I):

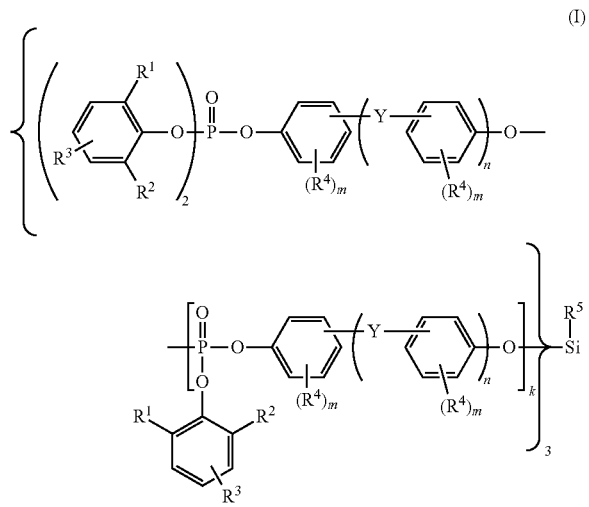

wherein $R^1$ and $R^2$ are the same or different and represent $C_1$-$C_5$ alkyl; $R^3$ and $R^4$ are the same or different and represent hydrogen, $C_1$-$C_5$ alkyl; $R^5$ is aryl or $C_1$-$C_5$ alkyl; Y is a linking bond containing —$CH_2$—, —$C(CH_3)_2$—, —S—, —$SO_2$—, —O—, —CO—, or —N=N—; m is an integer from 0 to 4; n is 0 or 1 and k is an integer from 0 to 9.

22 Claims, No Drawings

ORGANIC SILICON PHOSPHATE AND FABRICATION METHOD THEREOF

CROSS REFERENCE TO RELATED APPLICATIONS

This application claims priority of Taiwan Patent Application No. 098144938, filed on Dec. 25, 2009, the entirety of which is incorporated by reference herein.

BACKGROUND OF THE INVENTION

1. Field of the Invention

The present invention relates to a phosphate compound, and in particular relates to an organic silicon phosphate and fabrication method thereof.

2. Description of the Related Art

There are two kinds of flame retardants: inorganic and organic types. Compared with organic type flame retardant, higher amounts of the inorganic flame retardants must be added to the resin. However, when the addition of inorganic flame retardants is too high, the physical properties of resin deteriorate. Organic flame retardants come in two types; halogen and phosphorus. However, because the halogen-type flame retardants emit toxic gas and smog during fire, many efforts have been devoted towards developing the phosphorous type flame retardants.

The flame retardant effect of the phosphorus type depends on the amount of phosphorous content. Further, the mixing of flame retardants and resin using a heat-press process requires high temperature. Therefore, there is a need to develop a phosphorous type flame retardant having high phosphorous content and high thermal stability.

Monomer-types of phosphorous flame retardant, such as triphenyl phosphate (TPP) or tricresyl phosphate (TCP) was initially developed. However, because the major components of the monomer-type phosphorus flame retardant has a low molecular weight, it easily evaporates and causes environmental pollution. As a result, condensed phosphoric ester has been developed. Referring to U.S. Pat. Nos. 6,319,432, 6,605,736, 6,605,737 and 6613928, these patents disclose the fabrication methods of the condensed phosphoric ester, wherein the amounts of the low molecular compounds, which easily evaporate, are reduced.

Organic silane material retains the advantages of both the organic and the inorganic material. It is resistant to high and low temperature, it has excellent electrical insulating properties, high chemical stability and good durable properties. JP patent 2000-256378 disclose a phosphate containing silicon having good flame retardant properties and high thermal stability.

Accordingly, there is a need to develop an organic silicon phosphate which not only have the advantages of the organic silicon but also has high phosphorous content and high thermal stability.

BRIEF SUMMARY OF THE INVENTION

The invention provides an organic silicon phosphate of formula (I):

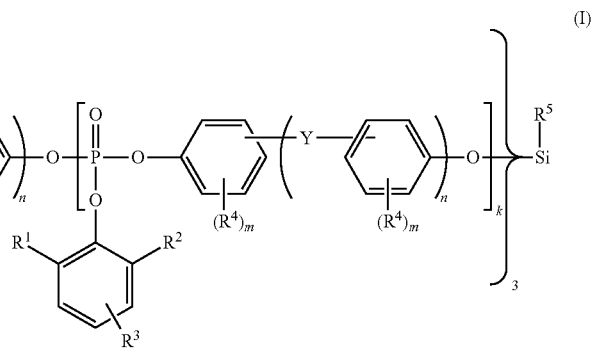

wherein $R^1$ and $R^2$ are the same or different and represent $C_1$-$C_5$ alkyl; $R^3$ and $R^4$ are the same or different and represent hydrogen, $C_1$-$C_5$ alkyl; $R^5$ is aryl or $C_1$-$C_5$ alkyl; Y is a linking bond containing —$CH_2$—, —$C(CH_3)_2$—, —S—, —$SO_2$—, —O—, —CO—, or —N=N—; m is an integer from 0 to 4; n is 0 or 1 and k is an integer from 0 to 9.

The invention also provides a fabrication method for an organic silicon phosphate, comprising: (a) reacting phenol of formula (III) with phosphoryl chloride with a molar ratio of 2:(1-1.2); (b) reacting the product from step (a) with divalent phenol of formula (IV-1), (IV-2), or (IV-3) with a molar ratio of 1:1; and (c) reacting the product from step (b) with organic silane with a molar ratio of 1:(0.01-1) to obtain the organic silicon phosphate of formula (I),

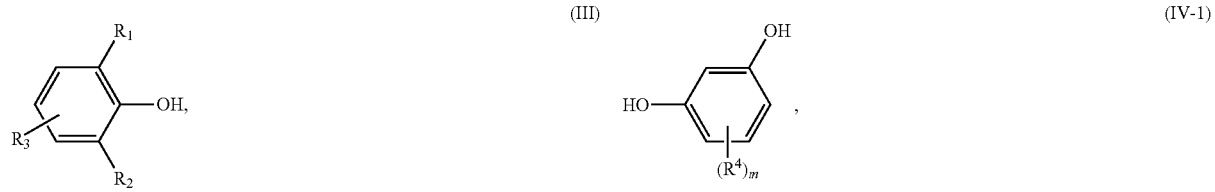

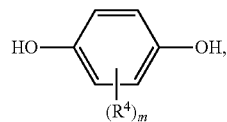
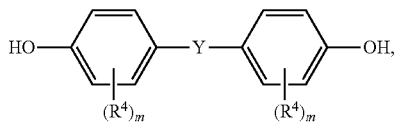

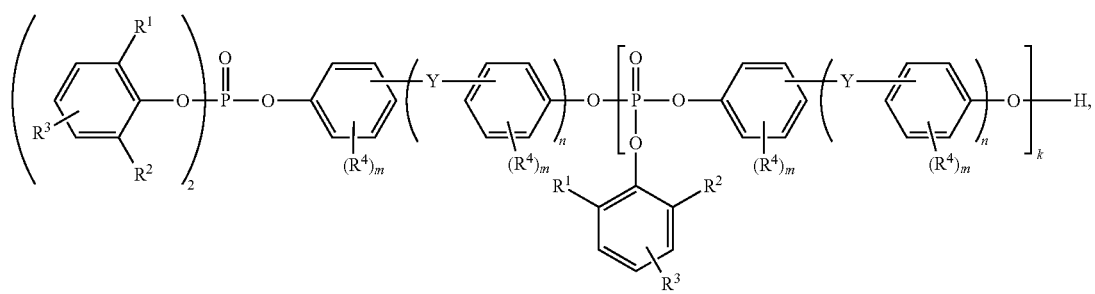

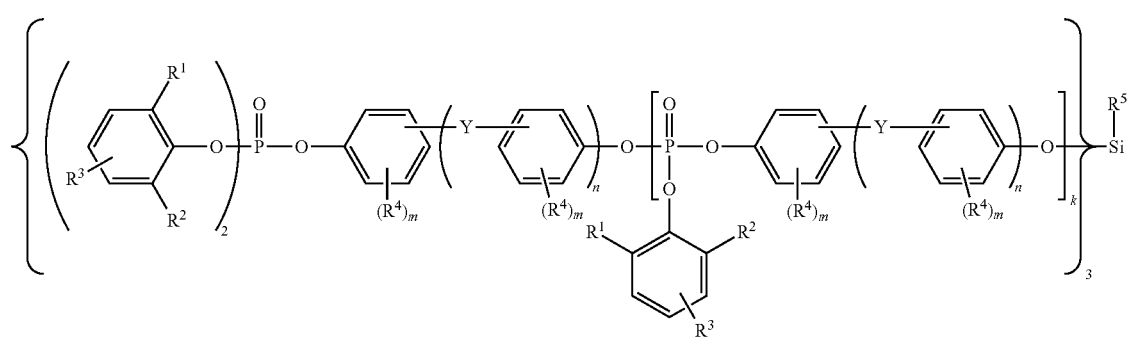

wherein $R^1$ and $R^2$ are the same or different and represent $C_1$-$C_5$ alkyl; $R^3$ and $R^4$ are the same or different and represent hydrogen, $C_1$-$C_5$ alkyl; $R^5$ is aryl or $C_1$-$C_5$ alkyl; Y is a liking bond containing —$CH_2$—, —$C(CH_3)_2$—, —S—, —$SO_2$—, —O—, —CO—, or —N=N—, m is an integer from 0 to 4; n is 0 or 1 and k is an integer from 0 to 9.

A detailed description is given in the following embodiments with reference to the accompanying drawings.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides an organic silicon phosphate having formula (I), wherein the organic silicon phosphate contains the components of organic silicon and has a tri-substituted organic silicon structure.

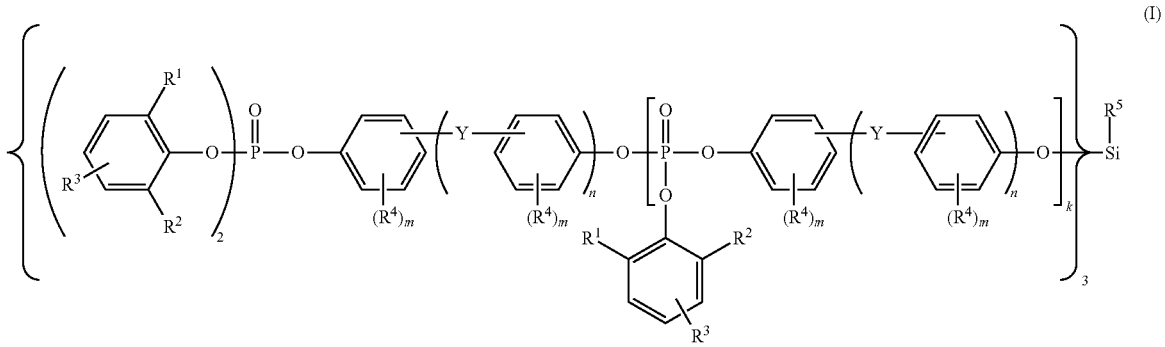

wherein $R^1$ and $R^2$ are the same or different and represent $C_1$-$C_5$ alkyl; $R^3$ and $R^4$ are the same or different and represent hydrogen, $C_1$-$C_5$ alkyl; $R^5$ is aryl or $C_1$-$C_5$ alkyl; Y is a liking bond containing —$CH_2$—, —$C(CH_3)_2$—, —S—, —$SO_2$—, —O—, —CO—, or —N=N—; m is an integer from 0 to 4; n is 0 or 1 and k is an integer from 0 to 9

In one embodiment, n=0. In another embodiment, k=0. In yet another embodiment, $R^5$ is phenyl.

In one embodiment, when $R^1$ and $R^2$ are methyl; $R^3$ is hydrogen; $R^5$ is phenyl; m=0; n=0; k=0; the organic silicon phosphate has formula (II):

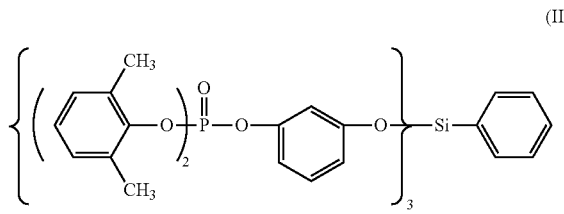

(II)

In another embodiment, when $R^1$, $R^2$ and $R^3$ are methyl; $R^5$ is phenyl; m=0; n=1; Y is —SO$_2$—; k=0; the organic silicon phosphate has the following structure:

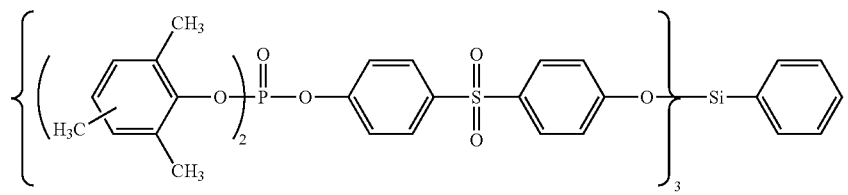

In yet another embodiment, when $R^1$, $R^2$ and $R^3$ are methyl; $R^5$ is phenyl; m=0; n=0; k=1; the organic silicon phosphate has the following formula:

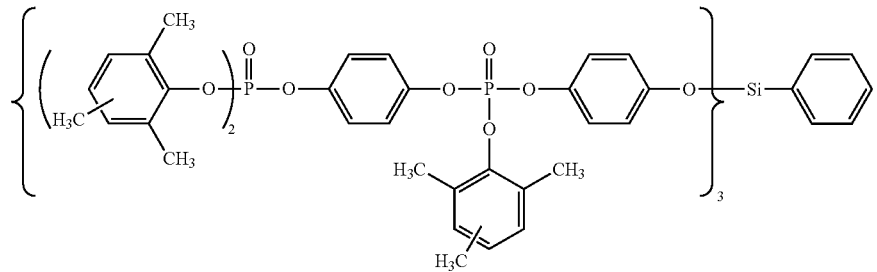

In yet another embodiment, when $R^1$, $R^2$ and $R^3$ are methyl; $R^5$ is phenyl; m=0; n=1; Y is —CH$_2$—; k=1; the organic silicon phosphate has the following formula:

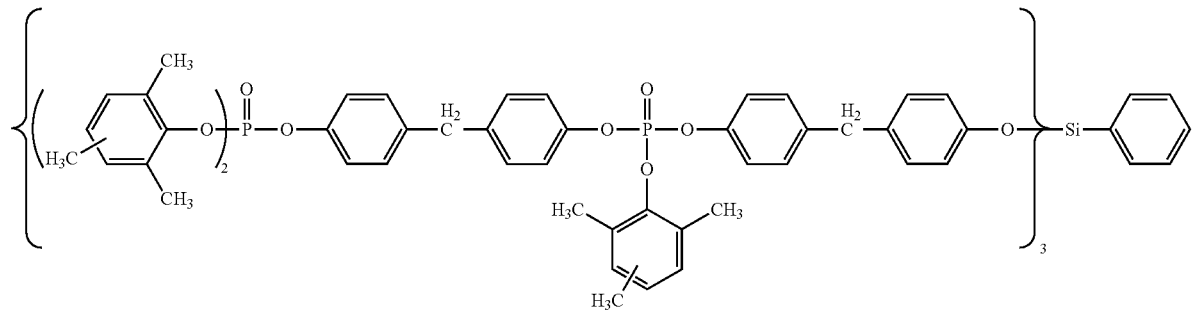

The organic silicon phosphate of the invention is an oligopolymer and has a molecular weight of about 1000-1500, preferably 1200-1300.

Note that prior art (JP 2000-256378) provided a bi-substituted organic silicon phosphate having a lower phosphorus content (about 5 wt %) and produced many by-products (such as organic salts) during the synthetic process. Thus, more complicated purification and post-treatment steps are needed to remove the unwanted by-products to obtain the highly purified product. Compared with the prior art, the phosphorus content of tri-substituted organic silicon phosphate of the invention is larger than 5 wt %, preferably 7 wt %, and it increases with the increase of k in formula (I). The high phosphorus content of organic silicon phosphate of the invention is obtained by simple water washing and neutralization steps, no complicated purification steps are necessary. Thus, the cost will be reduced.

Additionally, the organic silicon phosphate of the invention has high phosphorous content to improve the flame retardant effect and has excellent thermal stability due to the original property of the organic silicon, even at high temperature.

The invention also provides a fabrication method for an organic silicon phosphate which comprises step (a) to (c). The fabrication method begins with step (a) in which phenol of formula (III) react with phosphoryl chloride (POCl$_3$) with a molar ratio of 2:(1-1.2) and the reaction is shown below:

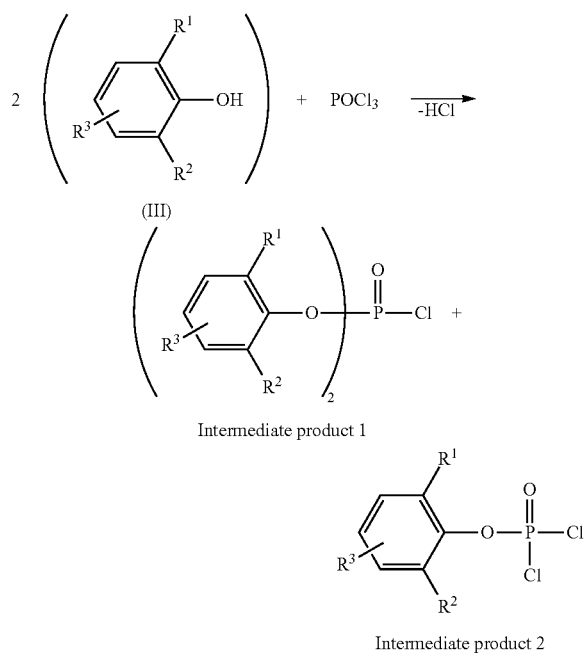

The Intermediate 1 and Intermediate 2 are obtained by the above reaction, wherein the Intermediate 1 is the primary product with a yield of about 80%-90%. Another by-product is hydrogen chloride gas (HCl) which is recycled by passing it through water under normal or reduced pressure.

The above-mentioned phenol comprises dimethylphenol, diethylphenol, 2-methyl-3-ethylphenol, 2-methyl-4-ethylphenol, 2-methyl-5-ethylphenol, 2-methyl-6-ethylphenol, 3-methyl-4-ethylphenol, 3-methyl-5-ethylphenol, 2-ethyl-3-methylphenol, 2-ethyl-4-methylphenol, 2-ethyl-5-methylphenol, 3-ethyl-4-methylphenol, di-n-propylphenol, diisopropylphenol, di-n-butylphenol, di-sec-butylphenol, di-tert-butylphenol, di-n-pentylphenol, diisopentylphenol, di-tert-pentylphenol, di-neo-pentylphenol, trimethylphenol, triethylphenol or tripropylphenol.

Step (a), further comprises mixing a Lewis acid as catalyst, such as metal halide. The examples of the metal halide (is liked) comprise anhydrous magnesium chloride (MgCl$_2$), anhydrous aluminum chloride (AlCl$_3$) or anhydrous titanium chloride (TiCl$_4$).

Step (a) is conducted at a temperature of about 80° C.-155° C., wherein the overall process of step (a) is preferably heated by three heating stages. The first heating stage is heated to about 80° C.-110° C., preferably about 90° C.-110° C., and more preferably about 100° C.-110° C. The second heating stage is heated to about 110° C.-135° C., preferably about 120° C.-135° C., and more preferably about 130° C.-135° C. The third heating stage is heated to about 135° C.-155° C., preferably about 145° C.-155° C., and more preferably about 150° C.-155° C.

Step (a) is conducted for about 3 to 27 hours and the process is divided into three stages to correspond to the three heating stages. The first heating stage is about 1 to 4 hours, and preferably about 2 hours-3 hours. The second heating stage lasts about 1 to 4 hours, and preferably about 2 hours-3 hours. The third heating stage requires about 1 to −20 hours, and preferably about 4 to 12 hours.

The fabrication step continues with step (b) in which Intermediate 1 and Intermediate 2 from step (a) are reacted with a divalent phenol of formula (IV-1), (IV-2), or (IV-3) with a molar ratio of 1:1 to obtain a compound of formula (V),

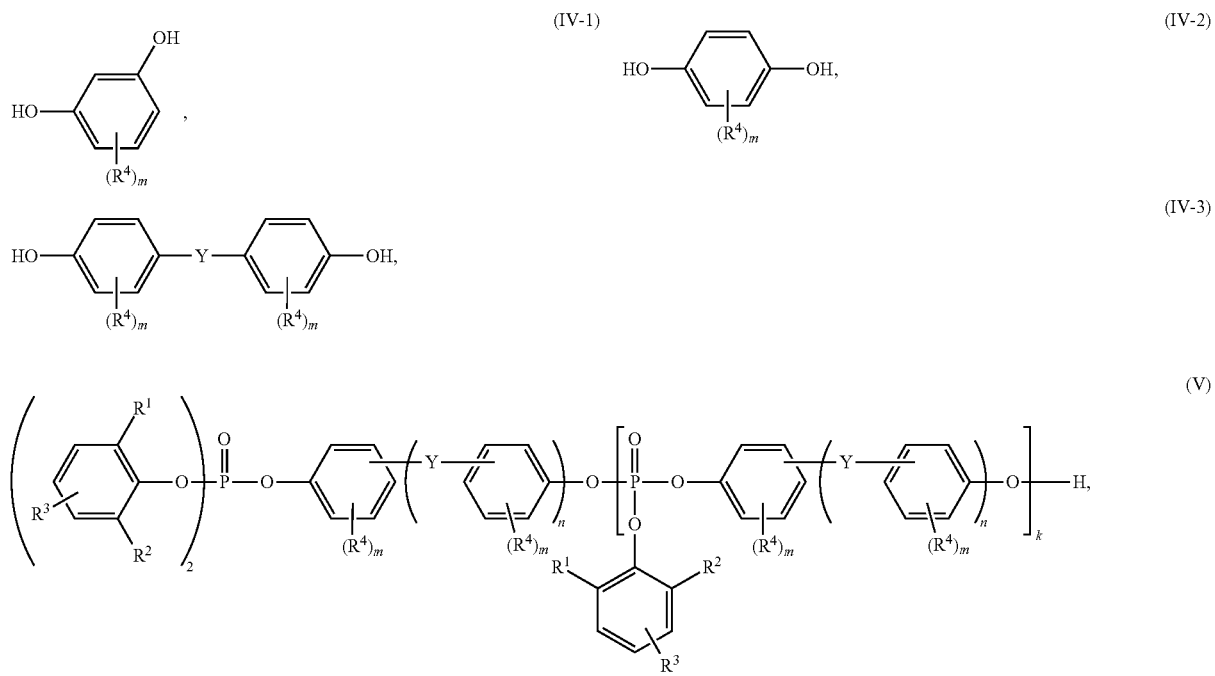

wherein $R^4$ are the same or different and represent hydrogen, $C_1$-$C_5$ alkyl; Y is a linking bond containing —$CH_2$—, —$C(CH_3)_2$—, —S—, —$SO_2$—, —O—, —CO—, or —N=N—; m is an integer from 0 to 4; n is 0 or 1 and k is an integer from 0 to 9.

Note that Intermediate 1 from step (a) has one chloride representing one substituted site and Intermediate 2 has two chloride representing two substituted sites. Thus, when Intermediate 1 and Intermediate 2 are reacted with the divalent phenol, the Intermediate 1 can stop the substitution reaction. The left side structure of formula (V) is synthesized by reacting Intermediate 1 with divalent phenol, and the numbers of n and k depend on the degree of reaction of Intermediate 1 and bivalent phenol. For example, the numbers of n and k (is raised) increase with the yield of Intermediate 2. Additionally, an unreacted hydroxyl group in formula (V) is used to react with organic silane in the sequential reaction.

The above-mentioned divalent phenol in step (b) comprises o-, m-, p-dihydroxybenzene, 4,4'-biphenol, 2,2-bis-(4-hydroxyphenyl)propane (bisphenol A), 4,4'-methylene bisphenol (bisphenol F), 4,4-sulfonul bisphenol (bisphenol S), 2,2-bis(4-hydroxyphenyl)butane, 1,1-bis(4-hydroxyphenyl)cyclohexane or 2,2-bis(3,5-dichloro-4-hydroxypennyl) propane. However, the divalent phenol are not limited to the divalent phenol mentioned herein, other divalent phenol which have two hydroxyl group are included within the scope of the invention.

Step (b) is conducted at a temperature of about 90° C.-140° C. for 2 hours-24 ours, and preferably about 100° C.-120° C. for about 10 hours-14 hours.

Then, the fabrication step continues with step (c) in which the products from step (b) are reacted with organic silane with a molar ratio of 1:(0.01-1) to obtain the organic silicon phosphate of formula (I). The organic silane in step (c) comprises phenyltrichloro silane, methyltrichloro silane, ethyltrichloro silane, n-propyltrichloro silane, isopropyltrichloro silane, n-butyltrichloro silane, isobutyltrichloro silane, sec-butyltrichloro silane, tert-butyltrichloro silane, n-pentyltrichloro silane, isopentyltrichloro silane, tert-pentyltrichloro silane or neo-pentyltrichloro silane.

Step (c) is conducted at a temperature of about 80° C.-160° C., wherein the overall process of step (c) is preferably heated by three heating stages. The first heating stage is heated to about 80° C.-120° C., preferably about 90° C.-120° C., and more preferably about 100° C.-120° C. The second heating stage is heated to about 120° C.-140° C., and preferably about 130° C.-140° C. The third heating stage is heated to about 140° C.-160° C., and preferably about 150° C.-160° C.

Step (c) is conducted for about 2 to 22 hours and the process is divided into three stages to correspond with the three heating stages. The first heating stage lasts for about 1 to 4 hours, and preferably about 2 to 3 hours. The second heating stage is heated for about 1 to 4 hours, and preferably about 2 to 3 hours. The third heating stage lasts for about 1 to 14 hours, and preferably about 8 hours-12 hours.

The above-mentioned step (a), (b) and (c) further comprise mixing a solvent to facilitate the reaction, wherein the solvent comprises toluene, o-, m-, p-xylene or 1,2,3-, 1,2,4-, 1,3,5-trimethylbenzene. For example, about 5 g-50 g of solvent is added into each molar of phosphoryl chloride ($POCl_3$).

The final product of formula (I) is obtained by undertaking step (a) to (c), wherein the primary product (yield: 50%-85%) has the following structure:

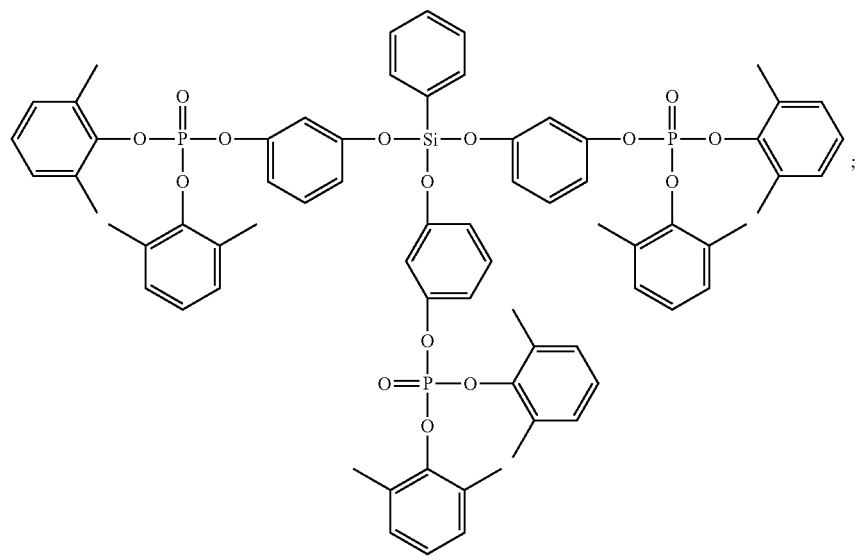

and secondary product (yield: 10%-50%) has the following structure:

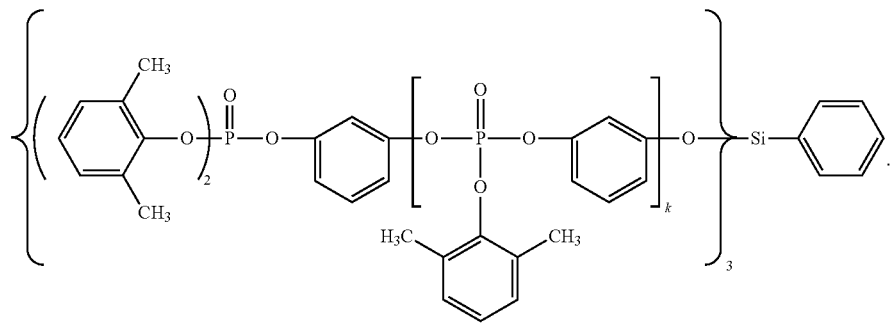

The impurities (such as unreacted compounds, catalyst remains or HCl gas) from the above steps are removed by acid washing, base washing, water washing or distillation under reduced pressure. In the acid washing method, acids such as hydrochloric acid, acetic acid, oxalic acid, sulfuric acid, phosphoric acid, or nitric acid are used. In the base washing method, the bases such as sodium hydroxide, potassium hydroxide, sodium carbonate or sodium bicarbonate are used.

When it is necessary to prevent the resultant product from being colored, a phosphrous-based compound such as triphenyl phosphate or tris(2,6-di-t-butyl) phosphate; a hindered phenol-based compound such as 2,6-di-t-butyl-p-creol (BHT) or 2-methyl-6-t-butyl-p-cresol; or the like can be added as a coloring prevention agent.

The organic silicon phosphate of the invention, having high phosphorus content and thermal stability, can be added into various thermoplastic resins or thermosetting resins to serve as an effective flame retardant. The thermoplastic resins include: polystyrene-based resin, polyamide-based resin, polyester-based resin or polycarbonated-based resin; and the thermosetting resins such as epoxy-based resin, phenol-based resin, urea-based resin or polyurethane.

In one embodiment, at least 29 wt % of the organic silicon phosphate of the invention is added into the epoxy to pass UL 94 (Underwriters Laboratory) classification V0 flammability testing standards.

EXAMPLE

Example 1

244 g (2.00 mol) of 2,6-dimethyl phenol, 7.03 g (0.07 mol) of anhydrous magnesium chloride ($MgCl_2$), 160 g (1.04 mol) of phosphoryl chloride ($POCl_3$) and 10 g of toluene were mixed in a four-necked bottle having a stir bar, a temperature meter, a condensed column for absorption of hydrogen chloride gas and a drop funnel. The mixture was gradually heated to 110° C. for 2 hours while a lot of hydrogen chloride gas formed. Then, the mixture was heated at 130° C. for 2 hours, then up to 155° C. for 6 hours, and finally under a reduced pressure of 150 mmHg at 155° C. for 4 hours.

When the mixture cooled down to 100° C., 61 g (0.55 mol) of m-dihydroxybenzene, 1.5 g (0.01 mol) of anhydrous aluminum chloride ($AlCl_3$) and 10 g of xylene were added into the mixture. Then, after the mixture was heated to 120° C. for 12 hours, 7.5 g (0.03 mol) of phenyltrichloro silane was added into the mixture. The mixture was heated to 140° C. for 2 hours and then up to 155° C. for 2 hours, and finally under a reduced pressure of 150 mmHg at 155° C. for 4 hours.

After the mixture cooled down to 100° C., 800 g of butanone was added into the mixture and then cooled down to room temperature. The mixture was sequentially washed by distilled water, 1% of HCl solution, 1% of NaOH solution and distilled water to obtain light brown oil. The solvent in the oil was removed by distillation under reduced pressure to obtain 307 g brown oil product. (yield: 88%)

Example 2

244 g (2.00 mol) of 2,6-dimethyl phenol, 7.05 g (0.07 mol) of anhydrous magnesium chloride ($MgCl_2$), 160 g (1.04 mol) of phosphoryl chloride ($POCl_3$) and 10 g of toluene were mixed in a four-necked bottle having a stir bar, a temperature meter, a condensed column for absorption of hydrogen chloride gas and a drop funnel. The mixture was gradually heated to 110° C. for 2 hours, during this time, a lot of hydrogen chloride gas formed. Then, the mixture was heated to 130° C. for 2 hours, then up to 155° C. for 6 hours, and finally under a reduced pressure of 150 mmHg at 155° C. for 4 hours.

When the mixture cooled down to 100° C., 110 g (1.00 mol) of m-dihydroxybenzene, 3.3 g (0.02 mol) of anhydrous aluminum chloride ($AlCl_3$) and 10 g of xylene were added into the mixture. Then, after the mixture was heated to 120° C. for 12 hours, 70 g (0.33 mol) of phenyltrichloro silane was added into the mixture in one hour. The mixture was heated to 140° C. for 2 hours and then up to 155° C. for 2 hours, and finally under a reduced pressure of 150 mmHg at 155° C. for 4 hours.

After the mixture cooled down to 100° C., 800 g of butanone was added into the mixture, it was then allowed to cool down to room temperature. The mixture was sequentially washed with distilled water, 1% of HCl solution, 1% of NaOH solution and distilled water to obtain light orange oil. The solvent in the oil was removed by distillation under reduced pressure to obtain 370 g yellow-orange oil product. (yield: 85%)

Example 3

The compounds used in Example 3 are the same as those in Example 2, except that the amount of phenyltrichloro silane is changed to 106 g (0.5 mol). Finally, red oil product was obtained. (yield: 80%)

Example 4

The organic silicon phosphate in Example 2 was added into several commercial resins according to Table 1. The mixture passes UL 94 (Underwriters Laboratory) classification V0 flammability testing.

TABLE 1

| components | wt % |
|---|---|
| Example 2 | 29.02 |
| Nan Ya 704 (Nan Ya Plastics Corp.) | 28.90 |
| Nan Ya 128EL (Nan Ya Plastics Corp.) | 11.45 |
| Chang Chun 190A70 (Chang Chun Plastics Corp.) | 5.96 |
| DIC LA-7751 | 24.67 |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic silicon phosphate having the formula (I):

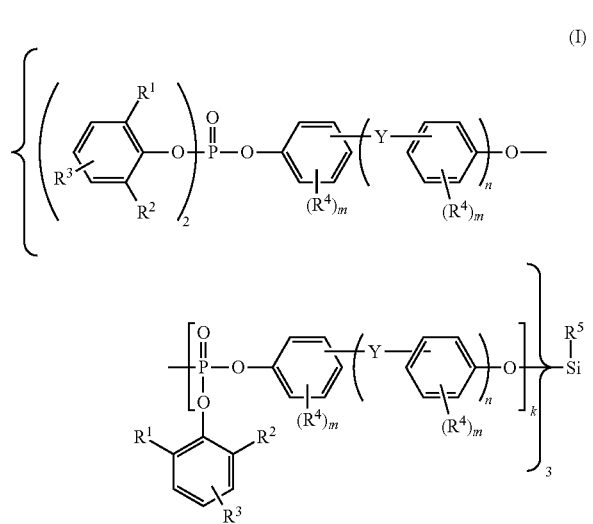

wherein $R^1$ and $R^2$ are the same or different and represent $C_1$-$C_5$ alkyl; $R^3$ and $R^4$ are the same or different and represent hydrogen, $C_1$-$C_5$ alkyl; $R^5$ is aryl or $C_1$-$C_5$ alkyl; Y is a linking bond containing —$CH_2$—, —$C(CH_3)_2$—, —S—, —O—, —CO—, or —N=N—; m is an integer from 0 to 4; n is 0 or 1 and k is an integer from 0 to 9.

2. The organic silicon phosphate as claimed in claim 1, wherein the organic silicon phosphate has a molecular weight of about 1000-1500.

3. The organic silicon phosphate as claimed in claim 1, wherein organic silicon phosphate is used as a flame retardant.

4. The organic silicon phosphate as claimed in claim 1, wherein n=0.

5. The organic silicon phosphate as claimed in claim 1, wherein k=0.

6. The organic silicon phosphate as claimed in claim 1, wherein $R^5$ is phenyl.

7. The organic silicon phosphate as claimed in claim 1, wherein the organic silicon phosphate has formula (II):

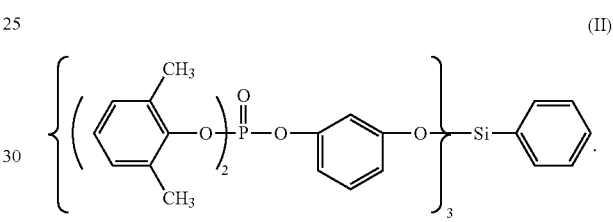

8. The organic silicon phosphate as claimed in claim 1, wherein the organic silicon phosphate has phosphorus content larger than 7 wt %.

9. A fabrication method for an organic silicon phosphate, comprising:
   (a) reacting phenol of formula (III) with phosphoryl chloride ($POCl_3$) with a molar ratio of 2:(1-1.2);
   (b) reacting the product from step (a) with divalent phenol of formula (IV-1), (IV-2), or (IV-3) with a molar ratio of 1:1; and
   (c) reacting the products from step (b) with organic silane with a molar ratio of 1:(0.01-1) to obtain the organic silicon phosphate of formula (I),

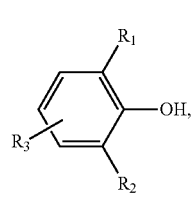

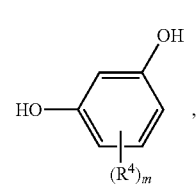

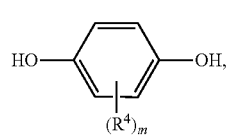

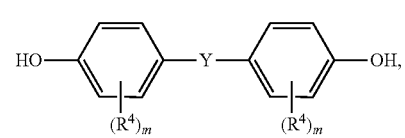

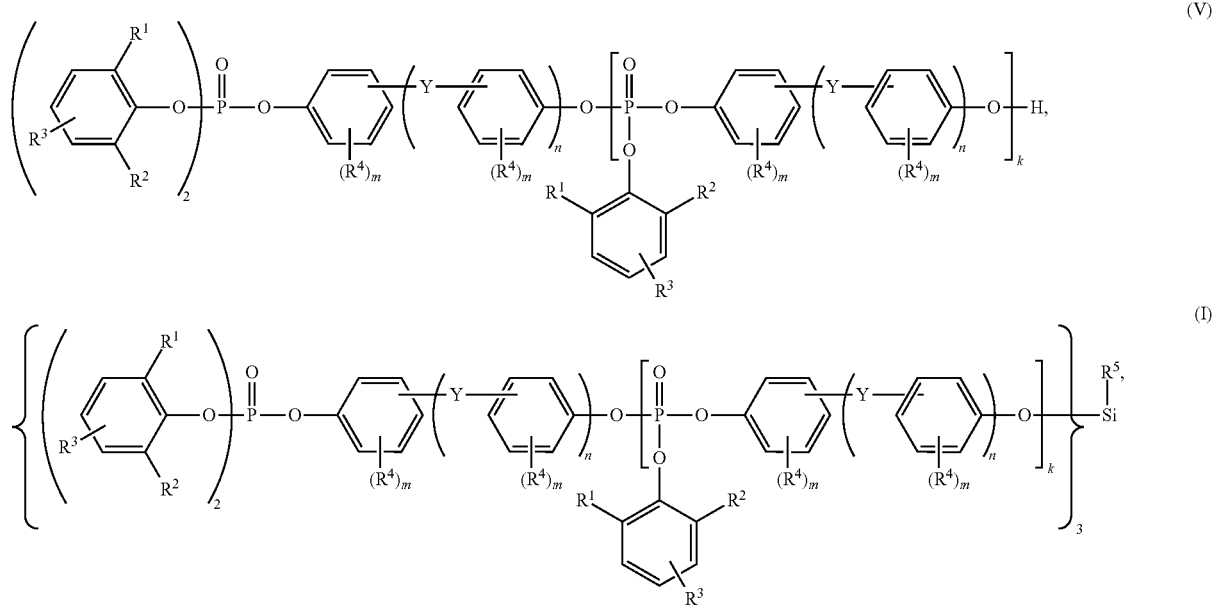

wherein $R^1$ and $R^2$ are the same or different and represent $C_1$-$C_5$ alkyl; $R^3$ and $R^4$ are the same or different and represent hydrogen, $C_1$-$C_5$ alkyl; $R^5$ is aryl or $C_1$-$C_5$ alkyl; Y is a linking bond containing —$CH_2$—, —$C(CH_3)_2$—, —S—, —$SO_2$—, —O—, —CO—, or —N=N—; m is an integer from 0 to 4; n is 0 or 1 and k is an integer from 0 to 9.

10. The fabrication method for an organic silicon phosphate as claimed in claim 9, in step (a) further comprising mixing a metal halide as a catalyst.

11. The fabrication method for an organic silicon phosphate as claimed in claim 10, wherein the metal halide comprises anhydrous magnesium chloride ($MgCl_2$), anhydrous aluminum chloride ($AlCl_3$) or titanium chloride ($TiCl_4$).

12. The fabrication method for an organic silicon phosphate as claimed in claim 9, wherein the phenol in step (a) comprises dimethylphenol, diethylphenol, 2-methyl-3-ethylphenol, 2-methyl-4-ethylphenol, 2-methyl-5-ethylphenol, 2-methyl-6-ethylphenol, 3-methyl-4-ethylphenol, 3-methyl-5-ethylphenol, 2-ethyl-3-methylphenol, 2-ethyl-4-methylphenol, 2-ethyl-5-methylphenol, 3-ethyl-4-methylphenol, di-n-propylphenol, diisopropylphenol, di-n-butylphenol, di-sec-butylphenol, di-tert-butylphenol, di-n-pentylphenol, diisopentylphenol, di-tert-pentylphenol, di-neo-pentylphenol, trimethylphenol, triethylphenol or tripropylphenol.

13. The fabrication method for an organic silicon phosphate as claimed in claim 9, wherein step (a) is conducted at a temperature of about 80° C.-155° C.

14. The fabrication method for an organic silicon phosphate as claimed in claim 9, wherein step (a) is conducted for about 3 to 27 hours.

15. The fabrication method for an organic silicon phosphate as claimed in claim 9, wherein the divalent phenol in step (b) comprises o-, m-, p-dihydroxybenzene, 4,4'-biphenol, 2,2-bis-(4-hydroxyphenyl)propane (bisphenol A), 4,4'-methylene bisphenol (bisphenol F), 4,4-sulfonul bisphenol (bisphenol S), 2,2-bis(4-hydroxyphenyl)butane, 1,1-bis(4-hydroxyphenyl)cyclohexane or 2,2-bis(3,5-dichloro-4-hydroxypennyl)propane.

16. The fabrication method for an organic silicon phosphate as claimed in claim 9, wherein step (b) is conducted at a temperature of about 90° C.-140° C.

17. The fabrication method for an organic silicon phosphate as claimed in claim 9, wherein step (b) is conducted for about 2 to 24 hours.

18. The fabrication method for an organic silicon phosphate as claimed in claim 9, wherein the organic silane in step (c) comprises phenyltrichloro silane, methyltrichloro silane, ethyltrichloro silane, n-propyltrichloro silane, isopropyltrichloro silane, n-butyltrichloro silane, isobutyltrichloro silane, sec-butyltrichloro silane, tert-butyltrichloro silane, n-pentyltrichloro silane, isopentyltrichloro silane, tert-pentyltrichloro silane or neo-pentyltrichloro silane.

19. The fabrication method for an organic silicon phosphate as claimed in claim 9, wherein step (c) is conducted at a temperature of about 80° C.-160° C.

20. The fabrication method for an organic silicon phosphate as claimed in claim 9, wherein step (c) is conducted for about 2 hours-22 hours.

21. The fabrication method for an organic silicon phosphate as claimed in claim 9, wherein step (a), (b), or (c) further comprises mixing a solvent.

22. The fabrication method for an organic silica phosphate as claimed in claim 21, wherein the solvent comprises toluene, o-, m-, p-xylene or 1,2,3-, 1,2,4-, 1,3,5-trimethylbenzene.

\* \* \* \* \*